United States Patent [19]

Tomoskozi et al.

[11] 4,429,123

[45] Jan. 31, 1984

[54] PREPARATION OF 6-KETO-7-OXO-PGF$_{1\alpha}$-DERIVATIVES

[75] Inventors: Istvan Tomoskozi, Budapest; Istvan Szekely, Dunakeszi; Karoly Kanai, Budapest; Peter Gyori, Budapest; Gabor Kovacs, Budapest, all of Hungary

[73] Assignee: Chinoin Gyogyszer es Vegyeszeti Termekek Gyara R.T., Budapest, Hungary

[21] Appl. No.: 368,016

[22] Filed: Apr. 13, 1982

[30] Foreign Application Priority Data

Apr. 14, 1981 [HU] Hungary .................................. 968

[51] Int. Cl.$^3$ ........................................... C07D 307/935
[52] U.S. Cl. .................................... 542/426; 549/465
[58] Field of Search ......................... 549/465; 542/426

[56] References Cited

PUBLICATIONS

Simonidesz et al., J.A.C.S., 100(21), 6756–6757, (1981).

Primary Examiner—Henry R. Jiles
Assistant Examiner—Bernard Dentz
Attorney, Agent, or Firm—Karl F. Ross; Herbert Dubno

[57] ABSTRACT

The present invention relates to a process for the preparation of compounds of the general Formula I

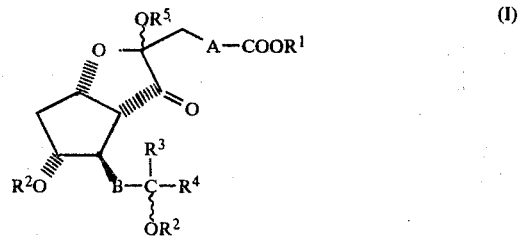

(wherein
A is a straight or branched chain alkylene group having 1–5 carbon atoms;
B is ethylene, Z or E vinylene, or ethynylene;
$R^1$ stands for hydrogen, an alkyl group having 1–5 carbon atoms or a pharmaceutically acceptable cation;
$R^2$ is hydrogen, an alkanoyl group having 1–5 carbon atoms or aroyl;

$R^3$ is hydrogen or methyl;
$R^4$ is a straight or branched chain alkyl group having 1–8 carbon atoms or an optionally monosubstituted aryloxymethyl group;
$R^5$ stands for hydrogen or an alkyl group having 1–5 carbon atoms)

which comprises oxidizing a compound of the Formula III, IV or V

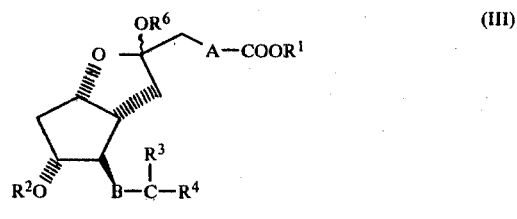

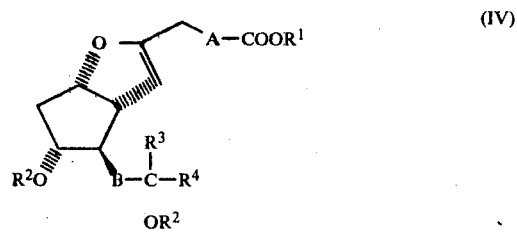

or

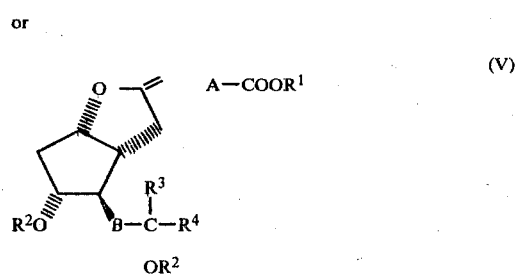

or a mixture thereof $R^6$ is hydrogen or an alkyl or alkanoyl group having 1–5 carbon atoms with a mild electrophilic oxidizing agent and if desired reacting the compound of the Formula I thus obtained wherein $R^5$ is hydrogen with an alkanol containing 1–5 carbon atoms in the presence of boron trifluoride etherate in a manner known per se to yield the corresponding compound of the Formula I in which $R^5$ is an alkyl group having 1–5 carbon atoms.

6 Claims, No Drawings

PREPARATION OF 6-KETO-7-OXO-PGF$_{1\alpha}$-DERIVATIVES

The present invention relates to a new, simple and economical process for the preparation of 6-keto-7-oxo-PGF$_{1\alpha}$ derivatives of the Formula I

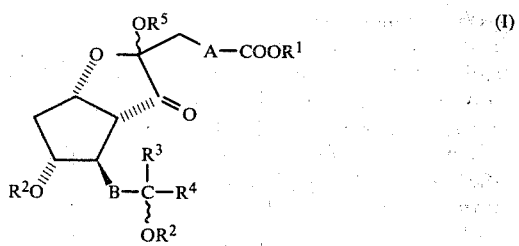

(wherein
- A is a straight or branched chain alkylene group having 1–5 carbon atoms;
- B is ethylene, Z or E vinylene, or ethynylene;
- R$^1$ stands for hydrogen, an alkyl group having 1–5 carbon atoms or a pharmaceutically acceptable cation;
- R$^2$ is hydrogen, an alkanoyl group having 1–5 carbon atoms or aroyl;
- R$^3$ is hydrogen or methyl;
- R$^4$ is a straight or branched chain alkyl group having 1–8 carbon atoms or an optionally monosubstituted aryloxymethyl group;
- R$^5$ stands for hydrogen or an alkyl group having 1 to 5 carbon atoms).

The compounds of the Formula I may be racemic or optically active; the substituents ~OR$^2$ and ~OR$^5$ marked with the sign "~" may be of α or β configuration.

The compounds of the Formula I possess biological activity per se, but their main utility is that they are useful intermediates in the preparation of 7-oxo-PGI$_2$ derivatives of the Formula

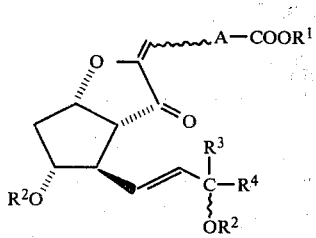

(wherein A, R$^1$, R$^2$, R$^3$ and R$^4$ have the same meaning as stated above).

The preparation of the compounds of the Formula II was first described in European Patent Application No. 0 031 426 (laid open on the July 8, 1981). These compounds exhibit strong and therapeutically useful blood aggregating inhibitory, de-aggregation, blood pressure decreasing, coronary dilatatory, antianginal, antidiarrhoeatic and cytoprotective effects and activate the the adenylate-cyclase enzyme system of blood platelets.

The compounds of the Formula II may be prepared from the compounds of Formula I by eliminating the elements of a compound of the Formula R$^5$OH (if R$^5$ is hydrogen, water is split off, while if R$^5$ stands for alkyl, an alcohol is removed).

The said procedures are described in the European patent application referred to above.

The present invention does not related directly to the preparation of the compounds of the Formula II.

The known methods for the preparation of the compounds of the Formula I is accompanied by serious drawbacks; the said methods are lengthy, circumstantial, complicated and have many reaction steps.

It has been surprisingly found that the compounds of the Formula I can be prepared in a simple manner with high yields by oxidizing a readily available known compound of the Formula

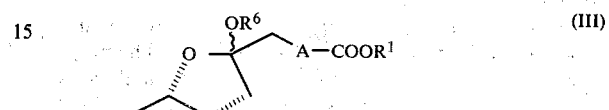

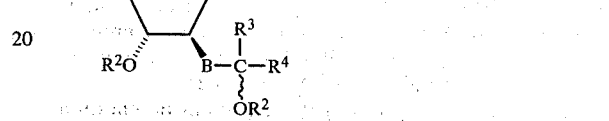

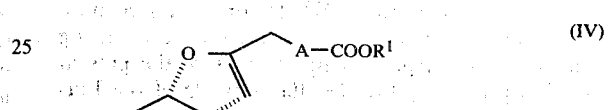

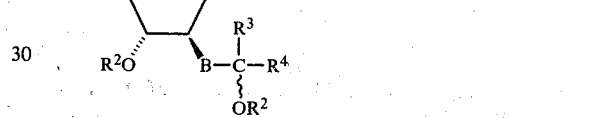

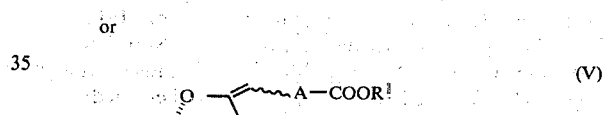

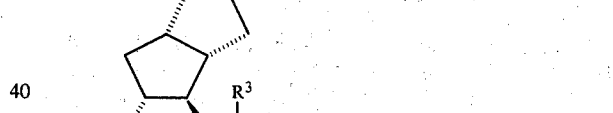

or

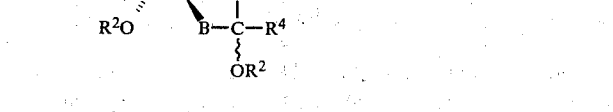

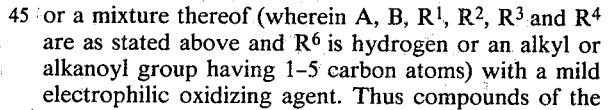

or a mixture thereof (wherein A, B, R$^1$, R$^2$, R$^3$ and R$^4$ are as stated above and R$^6$ is hydrogen or an alkyl or alkanoyl group having 1–5 carbon atoms) with a mild electrophilic oxidizing agent. Thus compounds of the Formula I, wherein R$^5$ is hydrogen, are obtained, which can be converted into the corresponding compounds of the Formula I, in which R$^5$ is an alkyl group having 1–5 carbon atoms, by reacting with an alkanol having 1–5 carbon atoms in the presence of boron trifluoride etherate.

The starting materials of the Formulae III, IV and V are known or can be prepared by processes analogous to the preparation of known compounds having similar structure.

The starting materials of the Formula III can be prepared from the corresponding PGF$_{2\alpha}$ derivatives by reacting the same in the presence of 1–2 mole of a thallium(III)compound—calculated per 1 mole of a PGF$_{2\alpha}$ derivative—with water or an alkanol having 1–5 carbon atoms. Depending on the reactant used, compounds of the Formula I are obtained in which R$^6$ stands for hydrogen or an alkyl group having 1–5 carbon atoms. (The said process is protected in our Hungarian patent application Ser. No. CI-1901.) The compounds of the Formula III, wherein $R^6$ is an alkanoyl group having 1–5 carbon atoms, can also prepared from the corresponding compounds of the Formula III, in which $R^6$ is hydrogen, by reacting the same with the anhydride or chloride of an alkanoic acid having 1–5 carbon atoms in the presence of a tertiary amine.

The most simple representative of the starting materials of the Formula IV is the $\Delta^6$-PGI$_1$ ($R^1$, $R^2$ and $R^3$ are hydrogen; A is —(CH$_2$)$_3$— B is E vinylene and $R^4$ is n-pentyl). The preparation of this compound is disclosed in J. Am. Chem. Soc. 100, 2547 and 7690 (1978). The other compounds of the Formula IV can be prepared in an analogous manner from the corresponding starting materials.

The most well-known member of the starting material group of the Formula V is prostacycline. The preparation of this compound and compounds analogous thereto is described in J. Am. Chem. Soc. 100, 7690 (1978) and DOS No. 2.702.553. The other compounds of the Formula V not disclosed in the cited references can be prepared by the methods described therein by using the corresponding starting materials.

According to the process of the present invention a compound of the Formula III, IV or V or a mixture thereof is oxidized with a mild electrophilic oxidizing agent. For this purpose in the process of the present invention preferably the selenium dioxide of the Formula VI

$$SeO_2 \qquad (VI)$$

can be used. The details of the application of this reagent are disclosed by M. J. Reich: Organoselenium Oxidations, Oxidation in Organic Chemistry, Editor: W. S. Trahanovsky, Academic Press, Inc., New York, 1978; and by D. L. J. Clive: Modern Organoselenium Chemistry, Tetrahedron Report, No. 50, Tetrahedron 34, 1049 (1978).

It has been found that the compounds of the Formula III, IV or V or mixtures thereof can be particularly preferably converted into the compounds of the Formula I by using 1–3 molar equivalent of selenium dioxide.

The reaction is preferably carried out in a mixture of water and an organic solvent. As an organic solvent, ether type solvents—e.g. dioxane, tetrahydrofurane or dimethoxy ethane—can be used.

The reaction temperature is about 25°–100° C., the reaction time may vary generally between 1 and 8 hours.

The compounds of the Formula I can easily be isolated from the reaction mixture by column chromatography.

The term "pharmaceutically acceptable cation" relates to mono-, di- or trivalent positive charges which do not cause any undesired side effects in the living organism in a dose which corresponds to the compounds of the Formula I. These may preferably be the following: cations of alkali metals (e.g. sodium, potassium or lithium), alkaline earth metals (e.g. calcium, magnesium), aluminum, ammonium and mono- or polyvalent ammonium ions derived from organic amines (e.g. tris-(hydroxy-methyl)-ammonium ion).

The term "Straight or branched chain alkyl groups having 1 to 5 carbon atoms" covers the methyl, ethyl, n-propyl, isopropyl, n-butyl, isobutyl, secondary butyl and tertiary butyl groups and all the isomeric amyl groups, the term "an alkyl group having 1–8 carbon atoms" encompasses in addition to the above alkyl groups also all the isomeric hexyl, heptyl and octyl groups.

The term "alkanoyl group having 1–5 carbon atoms" relates to the acyl radicals of alkanoic acids having 1–5 carbon atoms (e.g. formyl, acetyl, propionyl and all the isomeric butyryl and valerianyl groups). The term "aroyl group" covers unsubstituted or substituted benzoyl and naphthoyl groups, the aromatic ring may be substituted e.g. by halogen atom.

The term "optionally monosubstituted aryloxymethyl group" relates to phenoxymethyl and naphthyloxymethyl groups which can optionally bear a halogen substituent in any position of the aromatic ring.

Further details of the process claimed are to be found in the following Examples, without limiting the scope of protection to the said Examples.

EXAMPLE 1

Oxidation of 11,15-diacetyl-6-methoxy-PGI$_2$-methyl-ester with selenium dioxide 2.388 g (4.95 millimoles) of 11,15-diacetyl-6-methoxy-PGI$_1$-methyl-ester are dissolved in 10 ml of a 9:1 mixture of dioxane and water, whereupon 0.66 g (5.94 mmoles) of selenium dioxide are added in one portion under stirring at 80° C. The color of the solution becomes brownish red within 5 minutes because of the precipitation of selenium. Later the precipitated selenium forms black granules.

The reaction can be followed by means of thin layer chromatography. The $R_F$ value of the starting material and the end product is 0.46 and 0.29 respectively (on silica gel; eluent: 1:1 ethylacetate hexane mixture). The oxidation takes place within 1.5–2 hours. The reaction mixture is cooled to room temperature, whereupon 1.5 ml of triethyl amine are added, the mixture is diluted with 150 ml of ethyl acetate, washed in a separating funnel twice each time with 10 ml water each and 15 ml of a saturated sodium chloride solution and dried over magnesium sulfate. According to an alternative method the reaction mixture is worked up by clarifying with activated charcoal, filtration, cooling, dilution with 150 ml of ethyl acetate, washing in a separating funnel twice with 10 ml water each, 3 ml of a saturated sodium hydrogen carbonate solution, 20 ml of water and 15 ml of a saturated sodium chloride solution and drying over magnesium sulfate.

The solvent is distilled off and the residue is subjected to chromatography on a column containing 350 of silica gel and using a 1:1 mixture of n-hexane and ethyl acetate as eluent. Thus 1.52 g of 11,15-diacetyl-6-hydroxy-7-oxo-PGI$_1$-methylester are obtained in the form of a straw yellow viscous liquid. Yield: 63%.

$R_F$=0.29 (silica gel layer; 1:1 hexane-ethyl acetate mixture).

IR (film): $\nu_{max}$ 3250–3100 (broad band, OH) 1730 (C=O), cm$^{-1}$.

EXAMPLE 2

Oxidation of a mixture of 11,15-diacetyl-PGI$_2$-methyl-ester and 11,15-diacetyl-$\Delta^6$-PGI$_1$-methyl-ester with selenium dioxide 0.215 g (0.477 millimole) of a mixture of 11,15-diacetyl-PGI$_2$-methyl ester and 11,15-diacetyl-$\Delta^6$-PGI$_1$-methyl ester is dissolved in 2 ml of a 9:1 mixture of tetrahydrofurane and water. 0.106 g (0.954 mmoles) of seleniumdioxide is added under stirring in one portion and the reaction mixture is refluxed for 1.5-2 hours.

The reaction is followed by thin layer chromatography. The $R_F$ value of the starting material and the end product is 0.54 and 0.29 respectively (1:1 hexane-ethyl acetate mixture). The reaction having been completed the mixture is cooled to room temperature, 0.5 ml of triethyl amine is added, the mixture is diluted with 100 ml of ethyl acetate, washed subsequently twice with 10 ml of water each and 15 ml of a saturated sodium chloride solution and dried over magnesium sulfate.

The solvent is distilled off and the residue is subjected to chromatography on a column containing 30 g of silica gel and eluted with a 1:1 mixture of n-hexane and ethyl acetate. Thus 0.13 g of 11,15-diacetyl-6-hydroxy-7-oxo-PGI$_1$-methyl ester are obtained, yield: 59%. $R_F=0.28$ (1:1 mixture of hexane and ethyl acetate). IR (film): $\nu_{max}$3250-3100 (broad band, OH) 1730 (C=O) cm$^{-1}$.

EXAMPLE 3

Oxidation of 11,15-diacetyl-6-hydroxy-PGI$_1$-methyl-ester with selenium dioxide In an analogous manner to the previous Example 0.5 g (1 millimole) of 11,15-diacetyl-6-hydroxy-PGI$_1$-methyl ester is oxidized with 1.2 molar equivalents of selenium dioxide. Thus 0.29 g of 11,15-diacetyl-6-hydroxy-7-oxo-PGI$_1$-methyl ester are obtained. Yield: 58%. $R_F=0.20$.

EXAMPLE 4

Preparation of 11,15-diacetyl-6-methoxy-7-oxo-PGI$_1$-methyl ester 0.074 g (0.15 mmoles) of 11,15-diacetyl-6-hydroxy-7-oxo-PGI$_1$-methyl ester are dissolved in 3 ml of methanol whereupon at room temperature under stirring one drop of boron-trifluoride etherate is added. The reaction mixture is stirred for 15 minutes whereupone 1 ml of triethyl amine is added and the methanol is removed on a rotary evaporator in vacuo. The residual oil is subjected to column chromatography on 20 g silica gel and using n-hexane containing 30% of ethyl acetate and 0.5% of triethyl amine as eluent. Thus 0.056 g of the title compound are obtained. Yield: 73%. $R_F=0.34$ (in a 2:1 mixture of n-hexane and ethyl acetate, used twice).

What we claim is:

1. A process for the preparation of a compound of Formula I

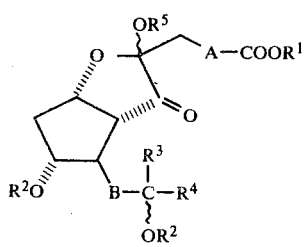

wherein

A is a straight or branched chain alkylene group having 1-5 carbon atoms;

B is ethylene, Z or E vinylene, or ethynylene;

$R^1$ is hydrogen, an alkyl group having 1-5 carbon atoms or a pharmaceutically acceptable cation;

$R^2$ is hydrogen, an alkanoyl group having 1-5 carbon atoms or aroyl;

$R^3$ is hydrogen or methyl;

$R^4$ is a straight or branched chain alkyl group having 1-8 carbon atoms or an optionally monosubstituted aryloxymethyl group; and $R^5$ is hydrogen which comprises oxidizing a compound of the Formula III, IV or V

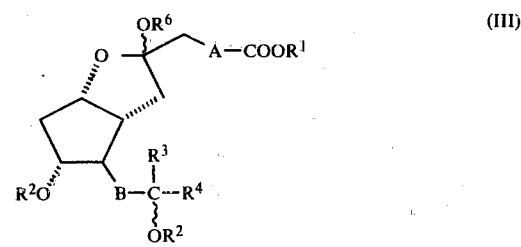

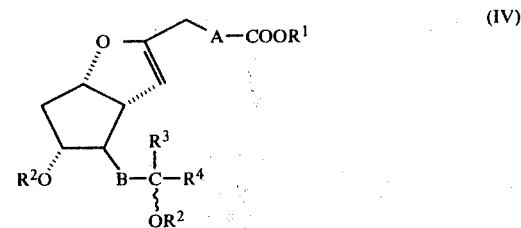

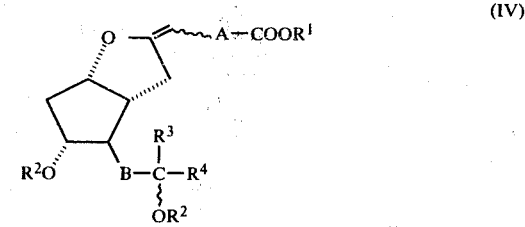

or a mixture thereof wherein $R^6$ is hydrogen or an alkyl or alkanoyl group having 1-5 carbon atoms with selenium dioxide to yield the compound of the formula (I).

2. The process defined in claim 1 which comprises using 1-3 molar equivalents of selenium dioxide as oxidizing agent.

3. The process defined in claim 1 which comprises carrying out the reaction in a mixture of water and an ether.

4. The process defined in claim 3 which comprises using a mixture of water and dioxane, water and tetrahydrofuran, or water and dimethoxyethane.

5. The process defined in claim 1 which comprises carrying out the reaction at a temperature between 20° C. and 100° C.

6. The process defined in claim 1 which further comprises the step of alkylating the compound of the formula (I) with an alkanol containing 1 to 5 carbon atoms in the presence of boron trifluoride etherate to yield the corresponding compound of the formula (I) where $R^5$ is an alkyl group having 1 to 5 carbon atoms.

* * * * *